United States Patent [19]

Kirschner et al.

[11] Patent Number: 5,453,245
[45] Date of Patent: Sep. 26, 1995

[54] METHOD OF DISINFECTING MEDICAL INSTRUMENTS

[75] Inventors: Ulrich Kirschner, Moerfelden-Walldorf; Frank Jethon, Bad Homburg, both of Germany

[73] Assignee: Fresenias AG, Germany

[21] Appl. No.: 57,202

[22] Filed: May 4, 1993

Related U.S. Application Data

[63] Continuation of Ser. No. 758,035, Sep. 12, 1991, abandoned.

[30] Foreign Application Priority Data

Sep. 13, 1990 [DE] Germany .................. 40 29 088.3

[51] Int. Cl.⁶ ........................................... A61L 2/16
[52] U.S. Cl. ............... 422/28; 422/1; 134/100.1; 210/636
[58] Field of Search ............ 422/1, 28; 134/42, 134/100.1; 210/140, 321.09, 636, 650, 651

[56] References Cited

U.S. PATENT DOCUMENTS

| | | | |
|---|---|---|---|
| 2,740,414 | 4/1956 | Moskow | 134/100.1 |
| 4,029,260 | 6/1977 | Herrick | 134/100.1 |
| 4,617,065 | 10/1986 | Sundheimer | 422/28 |
| 4,834,888 | 5/1989 | Polaschegg | 210/321.69 |
| 4,838,288 | 6/1989 | Wright et al. | 134/113 |
| 4,892,706 | 1/1990 | Kralovic et al. | 422/292 |
| 4,915,119 | 4/1990 | Franklin | 134/100.1 |
| 5,091,343 | 2/1992 | Schneider et al. | 422/292 |
| 5,217,698 | 6/1993 | Siegel et al. | 134/100.1 |

FOREIGN PATENT DOCUMENTS

| | | |
|---|---|---|
| 313478 | 2/1974 | Austria . |
| 0050864 | 5/1982 | European Pat. Off. . |
| 0097863 | 1/1984 | European Pat. Off. . |
| 0312104 | 4/1989 | European Pat. Off. . |

*Primary Examiner*—Robert J. Warden
*Assistant Examiner*—Theresa T. Snider
*Attorney, Agent, or Firm*—Panitch Schwarze Jacobs & Nadel

[57] ABSTRACT

A method of disinfecting medical instruments which includes positioning one or more medical instruments within a disinfecting chamber. A disinfectant and fresh water from a fresh water source are then mixed. The mixture of disinfectant and fresh water is then passed through a sterile filter having a water flux of more than 30 ml/hr-m²-mmHg into the disinfection chamber for engagement with one or more medical instruments in such a manner that all water and disinfectant engaging the one or more instruments passes through the sterile filter.

11 Claims, 1 Drawing Sheet

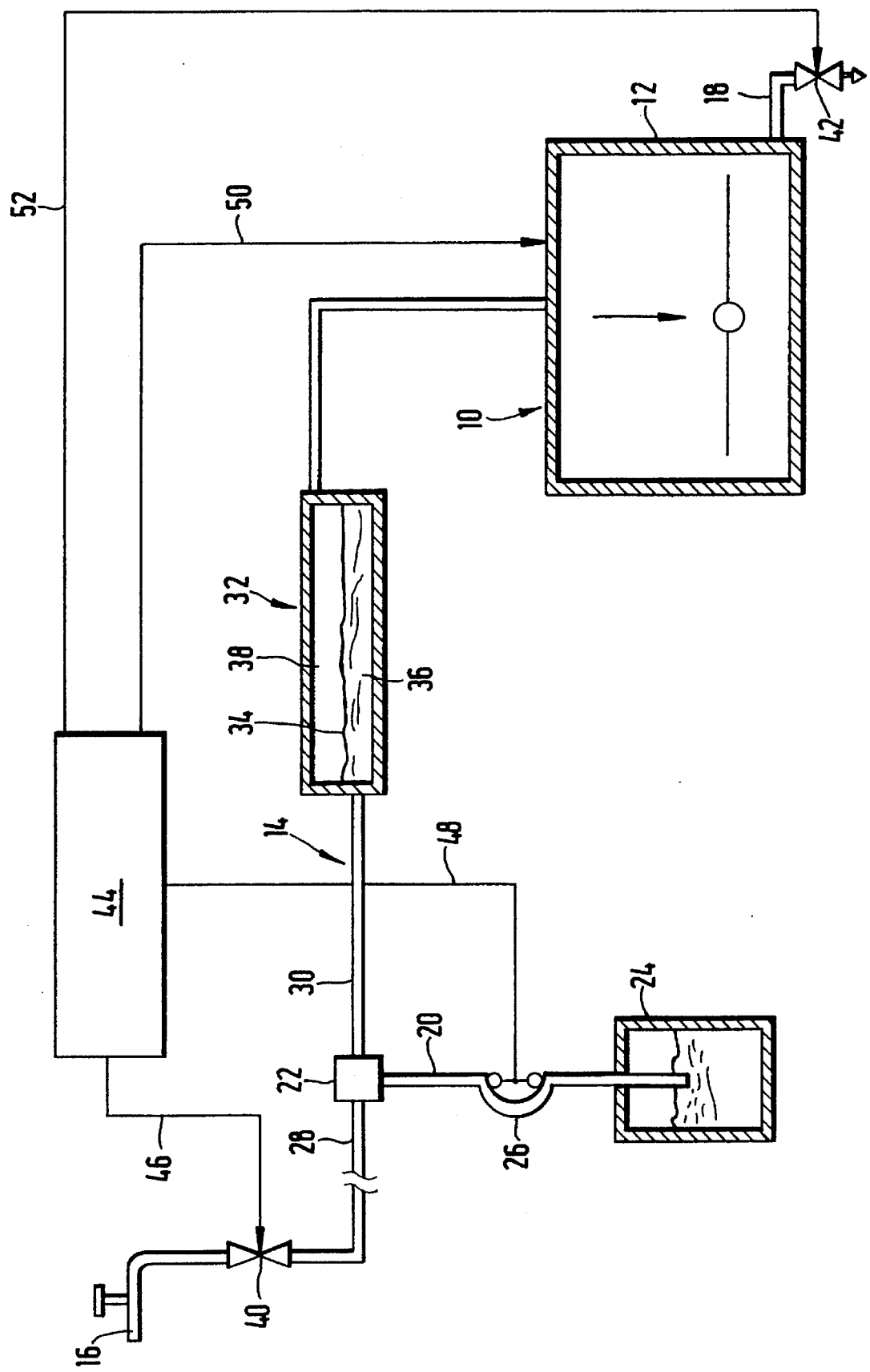

METHOD OF DISINFECTING MEDICAL INSTRUMENTS

This is a continuation of application Ser. No. 07/758,035, filed Sep. 12, 1991, now abandoned.

FIELD OF THE INVENTION

The invention concerns a medical disinfection instrument with a disinfection chamber, which is connected via a water inlet with a water source and which has a water outlet, wherein a disinfectant conduit leads to the water inlet and is connected at its other end with a reservoir for providing disinfectant with an engageable pump in the disinfectant conduit for transfer of the disinfectant.

BACKGROUND OF THE INVENTION

Apparatus of this type are generally used in the area of medicine for the sterilization and/or disinfection of operation apparatus, endoscopes, syringes, and the like, which cannot be sterilized and/or disinfected with hot air and/or hot steam at elevated temperatures. For this purpose a liquid disinfectant, usually in the form of a disinfectant concentrate, which is mixed with fresh water, is led to a disinfection chamber, in which the parts that are to be disinfected have been placed. There the disinfection takes place over a predetermined period of time, after which according to a certain program the used disinfectant is drained by means of the outlet. This is followed by a rinsing cycle for the removal of the disinfectant, after which the disinfected parts, if desired after drying, can be removed from the chamber.

Even though the pumped fresh water usually contains no germs, and almost the entire conduit has been rinsed with disinfectant, there are still problems with germs, especially Pseudomonas (*Pseudomonas aeruginosa*), which cannot be eliminated from the inlet area. This can lead to a new contamination of the already disinfected apparatus with the consequence that such contaminated apparatus can pose a danger to the patients to be treated.

Hence, the invention has the purpose of making available such a disinfection apparatus, which after the disinfection reliably excludes a contamination during the rinsing with water.

SUMMARY OF THE INVENTION

The solution of the problem is achieved in such a way that downstream of the mixing point of fresh water and disinfectant, a sterile filter with a water flux of more than 30 ml/hr-m$^2$-mmHg is connected into the water inlet conduit.

The apparatus of the invention has the advantage that the sterile filter which is situated prior of the disinfection chamber, reliably prevents a carry-over of germs into the disinfection chamber. Thereby the conduit section from the mixing point and the sterile filter remains sterile, as well as the conduit section which conducts disinfectant from the sterile filter to the disinfection chamber up until the introduction of fresh water after carrying out the disinfection process. Since there can be a release of germs from the conduit region upstream of the mixing point, these germs are only transported to the membrane of the sterile filter and there they are held back due to the much smaller pore size of the membrane, so that they cannot get into the sterile area downstream of the sterile filter.

Accordingly, all of the apparatus treated with liquid disinfectant in the disinfection chamber remain sterile, even after the rinsing with sterile fresh water, as it is received from the exit of the sterile filter.

As a sterile filter, a membrane filter is advantageously used, which allows a high water flux, for example more than 30 ml/hr-m$^2$-mmHg. Especially advantageous are high-flux-industrial filters, which are used with standard hemodialysis for sterile filtration. Such filters are hydrophilic due to their material properties and comprise, for example, polysulfone, which has been hydrophilized with the help of polyvinylpyrollidone, cellulose acetate, polyacrylonitrile and the like. They usually have a membrane surface between 1 and 3 m$^2$ and are usually provided in the form of a hollow fiber filter, which comprises approximately 9,000–10,000 hollow fibers in an essentially cylindrical housing. Such hollow fiber membranes have an inner diameter of approximately 0.2 mm, a wall thickness of approximately 20–30 µm and an average pore size less than 0.5 µm, especially less than 0.1 µm.

Especially advantageous is a hydrophilized and for industrial purposes modified polysulfone filter called F60 or F80 in the form of a hollow fiber filter, which is being used by the Applicant. In this form, the cylindrical shell, that has the hollow fibers, is sealed at its end with a sealant, in which the hollow fibers are imbedded. Such a sealant can, for example, comprise polyurethane that is hardened in situ, whereby afterwards through an ensuing partial cutting-off of the ends the fiber openings are opened again. Thereby, the aqueous disinfectant can be fed endwise into the hollow area (lumina) of the hollow fibers and can pass through through the pores of the hollow fibers into the space between the fibers in the housing and from there through an outlet opening conveyed to the disinfection chamber.

BRIEF DESCRIPTION OF THE DRAWING

The foregoing summary of the invention, as well as the following detailed description of the preferred embodiment, will be better understood when read in conjunction with the appended drawing. For the purpose of illustrating the invention, there is shown in the drawing an embodiment which is presently preferred, it being understood, however, that the invention is not limited to the specific arrangement and instrumentalities disclosed.

The single FIGURE shows a schematic flow diagram of a medical disinfection apparatus according to the invention.

DETAILED DESCRIPTION OF THE PREFERRED EMBODIMENT

In the FIGURE a disinfection apparatus 10 is shown, which has a disinfection chamber 12 which is equipped with standard (not pictured) treatment devices (spraying arms, revolving means and the like). Apparatus to be disinfected are received in this disinfection chamber. The disinfection chamber 12 is connected with a source of fresh water 16 by means of a water inlet 14 and has a water outlet 18 on the other side.

A disinfectant conduit 20 runs in to the water inlet where it forms mixing point 22. The other end of the disinfectant conduit 20 is connected with a disinfectant reservoir 24, which contains the disinfectant in the form of a concentrate. Also, a pump 26 is coupled into the disinfectant conduit 20, which pumps the disinfectant concentrate during usage to the mixing point 22 in the predetermined amount, but in the switched-off condition it blocks the disinfectant conduit.

The mixing point 22 thereby divides the water inlet 14 into a first conduit section 28, which is only impinged with fresh water, and into a second conduit section 30, which is flushed with completed disinfectant solution.

In the latter second conduit section a sterile filter 32 is located, whose interior is separated by a membrane 34 into a first filter chamber 36 and a second filter chamber 38. Moreover, the first filter chamber 36 is connected with the inlet part of the second conduit section 30, and the second filter chamber 38 with the outlet part of the second conduit section.

Further, the first conduit section 28 includes a water inlet valve 40, and the water outlet 18 includes an outlet valve 42. Finally, a control apparatus 44 is provided, that is connected by means of lines 46–52 with the water inlet valve 40, the pump 26, the disinfection chamber 12, and the outlet valve 42, respectively.

The disinfection apparatus 10 operates as follows:

For disinfection the disinfection chamber 12, which has been filled with the apparatus to be cleaned, is impinged with fresh disinfectant solution. For this the water inlet valve 40 is opened and the pump 26 is activated to convey the liquid disinfectant concentrate (for example, products of Fresenius AG sold under the trademarks "Ultrascope", "Puristeril", or "Sporcid M").

Since fresh water as well as the concentrate are conveyed to mixing point 22 in predetermined amounts, the composition and amount of the disinfectant solution are already known. The prepared disinfectant is pumped through the second conduit section 30 of the water inlet 14, thence through the sterile filter, and then conveyed to the disinfection chamber 12. After reaching a certain filling level in the disinfection chamber 12, the water inlet valve 40 and the pump 26 are deactivated with the consequence that the liquid disinfectant stays in the second conduit section and thereby effectively disinfects this entire section, including the sterile filter 32. After this the disinfection chamber 12 is put into operation, whereby the outlet valve 42 remains deactivated.

After the completion of the disinfection program, the outlet valve 42 is activated, so that the liquid disinfectant is drained from the disinfection chamber 12.

Next, the rinsing process takes place with fresh water by opening the water inlet valve 40, with the consequence that the entire water inlet 14 and the disinfection chamber 12 are rinsed with fresh water in a predetermined program. If there should be any remaining germs in the water inlet 14, they will certainly be held back by the sterile filter 32, so that the disinfection apparatus 10 remains sterile until the opening.

After the rinsing with fresh water, the regular program of drying and removal of the sterile apparatus takes place.

The present invention may be embodied in other specific forms without departing from the spirit or essential attributes thereof and, accordingly, reference should be made to the appended claims, rather than to the foregoing specification as indicating the scope of the invention.

We claim:

1. A method of disinfecting medical instruments, said method comprising the steps of:

positioning one or more medical instruments within a disinfecting chamber;

mixing a disinfectant and fresh water from a fresh water source; and passing the mixture of disinfectant and fresh water through a sterile filter having a water flux of more than 30 ml/hr-m$^2$-mmHg into the disinfection chamber for engagement with the one or more medical instruments in such a manner that all water and disinfectant engaging said one or more instruments passes through said sterile filter.

2. The method as recited in claim 1 wherein in the mixing step the mixing occurs in a common conduit.

3. The method as recited in claim 1 wherein in the mixing step the detergent is in concentrate form and the mixing occurs in a common conduit.

4. The method as recited in claim 1 further comprising the steps of:

passing fresh water from the fresh water source through the sterile filter into the disinfection chamber for engagement with the medical instruments to rinse the medical instruments.

5. The method as recited in claim 1 wherein said sterile filter is separated by a semi-permeable membrane into a first filter chamber and a second filter chamber, said first filter chamber being in fluid communication with said mixture of disinfectant and fresh water and said second filter chamber being in fluid communication with the disinfection chamber.

6. A method of disinfecting medical instruments, said method comprising the steps of:

positioning one or more medical instruments within a disinfecting chamber;

mixing a disinfectant and fresh water from a fresh water source;

passing the mixed disinfectant and fresh water through a sterile filter which comprises a plurality of microporous hollow fibers, which form a membrane having an average pore size of less than 0.5 μm, such that the sterile filter has a water flux of more than 30 ml/hr-m$^2$-mmHg; and passing the sterilized mixture of disinfectant and fresh water into the disinfection chamber for engagement with the one or more medical instruments in such a manner that all water and disinfectant engaging said one or more instruments passes through said sterile filter.

7. The method as recited in claim 6 wherein in the mixing step the mixing occurs in a common conduit.

8. The method as recited in claim 6 wherein in the mixing step the detergent is in concentrate form and the mixing occurs in a common conduit.

9. The method as recited in claim 6 further comprising the steps of:

passing fresh water from the fresh water source through the sterile filter into the disinfection chamber for engagement with the medical instruments to rinse the medical instruments.

10. The method as recited in claim 6 wherein said wherein said sterile filter is separated by a semi-permeable membrane into a first filter chamber and a second filter chamber, said first filter chamber being in fluid communication with said mixture of disinfectant and fresh water and said second filter chamber being in fluid communication with the disinfection chamber.

11. A method of disinfecting medical instruments comprising the steps of:

positioning one or more medical instruments within a disinfecting chamber;

mixing a disinfectant and fresh water from a fresh water source; and passing the mixture of disinfectant and fresh water through a sterile filter having a water flux of more than 30 ml/hr-m$^2$-mmHg into the disinfection chamber prior to engagement with the one or more medical instruments in the disinfecting chamber such that all water and disinfectant engaging said one or more medical instruments passes through said sterile filter.

* * * * *